United States Patent
Dardenne et al.

(10) Patent No.: US 12,290,325 B2
(45) Date of Patent: May 6, 2025

(54) AUTOMATIC DETERMINATION OF AN APPROPRIATE POSITIONING OF A PATIENT-SPECIFIC INSTRUMENTATION WITH A DEPTH CAMERA

(71) Applicants: INSTITUT NATIONAL DE LA SANTE ET DE LA RECHERCHE MEDICALE, Paris (FR); UNIVERSITE BREST BRETAGNE OCCIDENTALE, Brest (FR); CENTRE HOSPITALIER ET UNIVERSITAIRE DE BREST, Brest (FR); INSTITUT MINES TELECOM, Nantes (FR)

(72) Inventors: Guillaume Dardenne, Guipavas (FR); Salaheddine Sta, Brest (FR); Eric Stindel, Plougonvelin (FR); Thomas Gicquel, Guidel (FR)

(73) Assignees: INSTITUT NATIONAL DE LA SANTE ET DE LA RECHERCHE MEDICALE, Paris (FR); UNIVERSITE BREST BRETAGNE OCCIDENTALE, Brest (FR); CENTRE HOSPITALIER ET UNIVERSITAIRE DE BREST, Brest (FR); INSTITUT MINES TELECOM, Nantes (FR)

( * ) Notice: Subject to any disclaimer, the term of this patent is extended or adjusted under 35 U.S.C. 154(b) by 0 days.

(21) Appl. No.: 18/557,555

(22) PCT Filed: Apr. 14, 2022

(86) PCT No.: PCT/EP2022/060130
§ 371 (c)(1),
(2) Date: Oct. 26, 2023

(87) PCT Pub. No.: WO2022/228918
PCT Pub. Date: Nov. 3, 2022

(65) Prior Publication Data
US 2024/0225751 A1 Jul. 11, 2024

(30) Foreign Application Priority Data

Apr. 26, 2021 (EP) .................................. 21305535

(51) Int. Cl.
*A61B 34/20* (2016.01)
*A61B 34/10* (2016.01)
(Continued)

(52) U.S. Cl.
CPC ............ *A61B 34/20* (2016.02); *A61B 90/361* (2016.02); *G06T 7/0012* (2013.01);
(Continued)

(58) Field of Classification Search
CPC ........ A61B 2034/2055–2057; A61B 2090/064; A61B 2034/2065; A61B 2090/364;
(Continued)

(56) References Cited

U.S. PATENT DOCUMENTS

2018/0035966 A1* 2/2018 Merlet ...................... G06T 7/33
2019/0380792 A1* 12/2019 Poltaretskyi ............ G06F 30/20
(Continued)

FOREIGN PATENT DOCUMENTS

WO 2020216934 A1 10/2020
WO 2021003401 A1 1/2021
(Continued)

OTHER PUBLICATIONS

Foreign Communication from a Related Counterpart Application, International Search Report and Written Opinion dated Aug. 8, 2022, International Application No. PCT/EP2022/060130 filed on Apr. 14, 2022.

Primary Examiner — John D Li
(74) Attorney, Agent, or Firm — Conley Rose, P.C.

(57) ABSTRACT

Computer device (33) for determining an appropriate positioning of an instrumentation on a target bone area (200) according to a relative positioning (42) of said instrumentation to said target bone area defined by a surgical planning (32), said device comprising—an interface for receiving from a 3D camera (31) a depth map (41) of a captured scene
(Continued)

(310) comprising at least said target bone area; —computing means for determining a position element of said target bone area from said depth map; determining a second positioned shape (442) of said target bone area according to said relative positioning (42), and determining data (43) representative of said appropriate positioning on the base of said second positioned shape (442) and said position element; —a human-machine interface for providing said data.

6 Claims, 2 Drawing Sheets

(51) Int. Cl.
*A61B 90/00* (2016.01)
*G06T 7/00* (2017.01)
(52) U.S. Cl.
CPC . *A61B 2034/102* (2016.02); *A61B 2034/2057* (2016.02); *G06T 2207/10028* (2013.01); *G06T 2207/30008* (2013.01)

(58) Field of Classification Search
CPC . A61B 34/20; A61B 90/361; A61B 2034/102; A61B 2034/2068; G06T 7/75; G06T 7/0012; G06T 2207/10028; G06T 2207/30008
See application file for complete search history.

(56) References Cited

U.S. PATENT DOCUMENTS

| 2020/0129240 A1* | 4/2020 | Singh | A61B 34/10 |
| 2022/0117682 A1* | 4/2022 | Malackowski | A61B 34/30 |

FOREIGN PATENT DOCUMENTS

| WO | 2021071784 A1 | 4/2021 |
| WO | 2022228918 A1 | 11/2022 |

* cited by examiner

AUTOMATIC DETERMINATION OF AN APPROPRIATE POSITIONING OF A PATIENT-SPECIFIC INSTRUMENTATION WITH A DEPTH CAMERA

CROSS-REFERENCE TO RELATED APPLICATIONS

The present application is a filing under 35 U.S.C. 371 as the National Stage of International Application No. PCT/EP2022/060130, filed Apr. 14, 2022, entitled "AUTOMATIC DETERMINATION OF AN APPROPRIATE POSITIONING OF A PATIENT-SPECIFIC INSTRUMENTATION WITH A DEPTH CAMERA," which claims priority to European Application No. 21305535.3 filed with the European Patent Office on Apr. 26, 2021, both of which are incorporated herein by reference in their entirety for all purposes.

TECHNICAL FIELD

The invention relates to the technical domain of automatic monitoring of the positioning of an instrumentation like a patient surgery instrumentation, PSI, in particular during a computer-aided surgical procedure.

BACKGROUND

Computer-assisted surgery, and in particular computer-assisted orthopaedic surgery (CAOS), is a discipline where computer technology is applied pre-, intra- and/or post-operatively to improve the outcome of a surgical procedures.

In particular, such techniques allow to plan the component placement in advance, including determination of the appropriate component sizes; measure the intra-operative placement of the components in real time, making sure that the plan is adhered to.

Some proposals have been published regarding computer-assisted techniques guiding the surgeon in his/her gesture. These proposals rely on computerized stations embedding optical cameras so as to localize in real-time some markers placed on surgical instruments and/or on the bone structures. By comparing relative positions and orientations, the system can dynamically inform the surgeon about the accuracy of his/her gestures related to a plan, allowing him/her to correct any divergences.

Such techniques can be applied to diverse surgical procedures like arthroplasties of hip, knee, shoulder, or osteotomy, etc.

However, the cost and the burden and additional time of installing such proposals and, especially, accurately placing markers before the procedure jeopardize the generalized usage of these techniques. Indeed, positioning and fastening these markers on the adequate placement need some extra-stage which can elongate time of surgery procedure and also global costs.

More recent techniques make use of guiding instrumentation that are placed on the bone structure so as to guide the gestures of the surgeon.

In particular, it has been proposed to use Patient Specific Instrumentation, PSI, to better adapt to the specific morphology of the bone structures of the patient and improve the accuracy of the guiding provided by the instrumentation.

Articles like Ast M P, Nam D, Haas S B. "Patient-specific instrumentation for total knee arthroplasty: a review", Orthop Clin North Am 2012; 43:e17-22. 10.1016/j.ocl.2012.07.004, provide a review of the PSI techniques and demonstrate the importance of the accuracy of the surgeon's gestures during the surgical procedure, especially the cuts for further placing prosthesis.

These PSI are designed to be accurately adapted on the bone surface by planning in advance their shape from preoperative three-dimensional digital images of the implementation scene of the patient with either Computed Tomography (CT scan) or Magnetic Resonance Imaging (MRI), and to guide the gestures of the surgeon in the subsequent procedure, e.g. cuts in the bone structure for implanting a prosthesis.

Such techniques allow good accuracy and performances in placing prosthesis or other components in the optimal position, with costs lower than the "traditional" marking-based guiding.

However, some practical issues still limit a widespread use of PSI-based techniques. Indeed, as mentioned above, PSI are designed on the basis of images of the implantation site. And, all the required information cannot be visualized, for instance, in case of images provided by a CT, such images cannot correctly show osteophytes and cartilage covering articulation areas.

In consequence, the design of the PSI cannot take into account these osteophytes and cartilage, which may imply some inaccuracies when implanting the PSI on-site and, subsequently, when operating the required gestures by the surgeon as guided by the misplaced PSI.

The surgeon shall thus remove the cartilage in the area where the PSI shall be implanted, but, still, the resulting accuracy of this implantation results directly from the dexterity and skills of the surgeon. Some studies have demonstrated that in many cases the PSI was not well placed (i.e. according to the planning), which would result in deceptive post-procedure results.

Examples of such studies are Kunz M, Balaketheeswaran S, Ellis R E, Rudan J F. "The influence of osteophyte depiction in CT for patient specific guided hip resurfacing procedures", in Int. J. Comput. Assist. Radiol. Surg, 10(6), pp. 717-726, 2015, or Wu, X. D., Xiang, B. Y., Schotanus, M. G., Liu, Z. H., Chen, Y., & Huang, W. (2017). "CT-versus MRI-based patient-specific instrumentation for total knee arthroplasty: a systematic review and meta-analysis" in the surgeon, 15(6), 336-348.

Images provided by MRI allow to better show cartilage and osteophytes and allows better design of the PSI. However, MRI is still a costly option compared with scanner and not always easily reachable in clinical routine, which still obstructs the deployment of PSI-based techniques.

In additional, it has been reported in e.g. WOOLSON, Steven T., HARRIS, Alex H S, WAGNER, David W., et al. Component Alignment During Total Knee Arthroplasty with Use of Standard or Custom Instrumentation. J Bone Joint Surg Am, 2014, vol. 96, no 5, p. 366-372, that the position and/or orientation of the PSI may need to be adjusted during the procedure, so as to improve the results.

So far, however, no solution has been proposed to check during the surgical procedure the intraoperative position and orientation of the PSI according to a predetermined planning.

SUMMARY

Aims of the invention comprises ameliorating the current proposals for assisting surgeons in using PSI for surgical procedures.

In particular, embodiments of the invention allow to provide good accuracy in implanting the PSI (both in position and orientation) according to a predetermined planning, while minimizing the costs and preparation time, contrary to conventional navigation systems that requires additional markers, especially attached to the bone.

In a first example embodiment, a computer device is provided for determining an appropriate positioning of an instrumentation on a target bone area according to a relative positioning of said instrumentation to said target bone area defined by a surgical planning, said device comprising an interface for receiving from a 3D camera a depth map of a captured scene comprising at least said target bone area and said instrumentation;

computing means for determining a position element of said target bone area from said depth map, which may comprise a first positioned shape of said target bone area; determining a positioned shape of said instrumentation from said depth map, determining a second positioned shape of said target bone area according to said positioned shape and to said relative positioning, and determining data representative of said appropriate positioning on the base of said second positioned shape and said first positioned shape;

a human-machine interface for providing said data.

This embodiment may comprise other features, alone or in combination, such as:

said data comprises rigid transformation data reflecting error vectors between said first and second positioned shapes;

the computer is further configured to provide data comprising a distance map, from said second positioned shape and said first positioned shape.

the computer device is further adapted to determine at least one of said positioned shape of said instrumentation according to a Point-Pair Feature algorithm;

the computing means comprises at least one processor; and at least one memory including computer program code, the at least one memory and computer program code configured to, with the at least one processor, cause the performance of the computer device;

the instrumentation is a patient surgery instrumentation, PSI.

A second example embodiment of the invention relates to a system comprising a computer device as previously defined and a 3D camera.

Another example embodiment of the invention relates to a method for determining an appropriate positioning of an instrumentation on a target bone area according to a relative positioning of said instrumentation to said target bone area defined by a surgical planning, said method comprising capturing a depth map of a captured scene comprising at least said target bone area and said instrumentation, by a 3D camera;

determining a position element of said target bone area from said depth map which may comprise a first positioned shape of said target bone area;

determining a positioned shape of said instrumentation from said depth map, determining a second positioned shape of said target bone area according to said positioned shape and to said relative positioning;

determining data representative of said appropriate positioning on the base of said second positioned shape and said first positioned shape.

This embodiment may comprise other features, alone or in combination, such as:

said data comprises rigid transformation data reflecting error vectors between said first and second positioned shape;

said data comprises a distance map, from said second positioned shape and said first positioned shape;

said instrumentation is a patient surgery instrumentation, PSI.

Another example embodiment of the invention relates to a computer readable medium encoding a machine-executable program of instructions to perform the method as previously defined.

The determination of the appropriate positioning could simply allow checking whether the PSI is appropriately positioned or not.

BRIEF DESCRIPTION OF THE FIGURES

Some embodiments are now described, by way of example only, and with reference to the accompanying drawings, in which.

DESCRIPTION OF EMBODIMENTS

Figure 1:
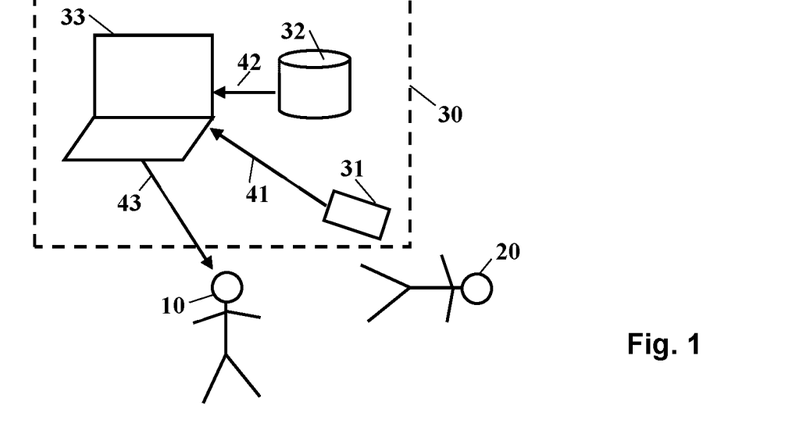
FIG. 1 schematically illustrates a possible context in which embodiments of the invention may be used.

In reference to FIG. 1, a surgeon 10 uses a computerized system 30 for performing a surgical procedure on a patient 20.

According to this embodiment, the computerized system 30 comprises a computer (or any similar device with similar functionalities) 33, a 3D-camera 31 and a database, or memory, 32.

The database or memory 32 is adapted to store a planning of the surgical procedure.

The memory can be local or remote to the computer 33.

They can be linked by any communication means available in the art, like for instance WiFi, Bluetooth or cellular radio network, or wired Ethernet link. The same may apply for the communication means between the 3D camera 31 and the computer 30.

The planning may define or specify various elements about the surgical procedure to be performed and in particular about the instrumentations to be implanted on a bone target area.

In particular, the planning may define the shape and the positioning of an instrumentation relatively to the target bone area. This planning takes into account the morphology of the target bone's structure.

Such a planning may be defined before the surgical procedure itself by capturing an image of the anatomical region of interest by a scanner or a MRI or any other techniques, onto which the surgeon or any other specialists can determine the suitable position for the PSI according to its medical and surgical skills to further correctly place the prosthesis.

The planned position comprises the position of its shape, i.e. of a set of feature points, so that both the location and the orientation of the instrumentation are determined, relatively to the bone structure onto which it shall be placed (i.e. the bone target area).

The Instrumentation can be a Patient Specific Instrumentation, PSI, or a standard instrumentation (i.e. not specific to a given patient).

PSI have been introduced recently in orthopaedic surgery and are mainly used to perform bony cuts in order to further place the implants. These instruments are designed according to the patient's anatomy observed from computed tomography (CT) or magnetic resonance imaging (MRI) and with a surgical planning. PSIs are placed during the surgical procedure by aligning their customized shape adapted to the bone's structure morphology of a patient.

The position (location and orientation) as defined during the planning phase can be stored in the memory 32, so that it can be transmitted, 42, to the computer device 33 when needed, e.g. during and/or after the procedure phase.

The 3D (Three Dimensions) camera 31 is adapted to provide a depth map of a captured scene comprising at least a part of a target bone area, i.e. the place where the instrumentation shall be placed. According to some embodiments (depending notably on the position of the camera with regard to the patient 20), the captured scene may be broader and comprises parts or totality of the instrumentation. It is only important that the captured scene comprises enough information to measure a relative positioning of the instrumentation with regard to the bone structure so that it can be later compared with the planned relative position 42.

Various models of 3D camera can be provided. In particular, 3D cameras may refer to:
  Range camera: a device which produces a depth map showing the distance to points in a scene from a specific point.
  Stereo camera: a type of camera with two or more lenses with separate image sensors or film frame for each lens, which allows the camera to simulate human binocular vision, and therefore capture three-dimensional images.
  Examples of range cameras include:
  Projected-light cameras: Kinect, Asus Xtion Pro Live, Ensenso, etc.
  Modulated-light time of flight: SR4000 (Swiss Ranger)
  Pulsed-light time of flight: Tiger Eye (Advanced Scientific Concepts, Inc.)
  Pulsed-light rotating scanner: Velodyne.

According to embodiments, the 3D camera is a RGBD camera. A RGBD camera combines the functions of a video camera, capturing a RGB (Red, Green, Blue) frame flow, with the functions of 3D sensors like a range camera as exemplified above. The 2 signals are combined so as to form RGB-D frame flow ("D" meaning "depth").

In the following, the term "3D camera" will reflect a device adapted to provide at least a depth map of a captured scene, and only optionally, a RGB vector for the points of the captured scene.

Experiments made by the inventors have shown that 3D cameras like Microsoft Azure Kinect and the Occipital Structure Core depth sensor outperform other tested devices and are preferred implementation means. In particular, this kind of camera is less sensible to lighting conditions which can significantly deteriorate images features and so the performance of the pose estimation algorithm.

It shall be noted that such devices are relatively low-cost and affordable for any Operation Room operator.

A depth map associates to each pixel, a depth value, i.e. a distance between the captured object and the sensor.

According to embodiments, a RGBD camera can be used. In such embodiments, a resulting data structure could be an array of pixels wherein each pixel is associated to colour value(s) and to a depth. The colour value may be based on the RGB (Red, Green, Blue) colorimetric model (in case of RGB-D cameras, for instance).

The captured depth map 41 can be transmitted to the computer device 33. This computed device 33 comprises appropriate interface to receive this depth map from the 3D camera 31.

The computer 33 may be a standard computer (desktop, laptop . . . ) or any other devices enabled to process data (tablets, smartphones . . . ), or even a collaboration of a local device (ensuring visualisation functions) and a remote platform handling the processing function.

The computer (or a local device of it) further comprises a Human-Machine Interface to display to the surgeon data representative of the appropriate positioning of the instrumentation, i.e. an accurate mapping of its actual position with the planned position.

This Man Machine Interface may comprise visualisation means so as to display various data, like images captured by the 3D camera, and other information determined by the method of the invention to guide the surgeon performing the surgery, including data representative of the appropriate positioning of the instrumentation.

Other type of Human-Machine Interface can also be provided, like:
  sound producing, for informing the surgeon about the accuracy of the position of the instrumentation in real time (and for instancing alarming it when the position is bad);
  Mixed Reality devices allowing the surgeon to visualize computer-produced data enriching the direct vision of the surgery;
  etc.

The data 43 provided to the surgeon may be in real-time, i.e. the video-flow of the 3D camera is continuously processed so as to refresh the data representative of the appropriate positioning of the instrumentation.

The data provided to the surgeon may also be only on demand of the surgeon, or at the end of the surgery, for instance.

As mentioned earlier, the 3D camera can be placed at different position (both location and orientation).

Figure 2A:
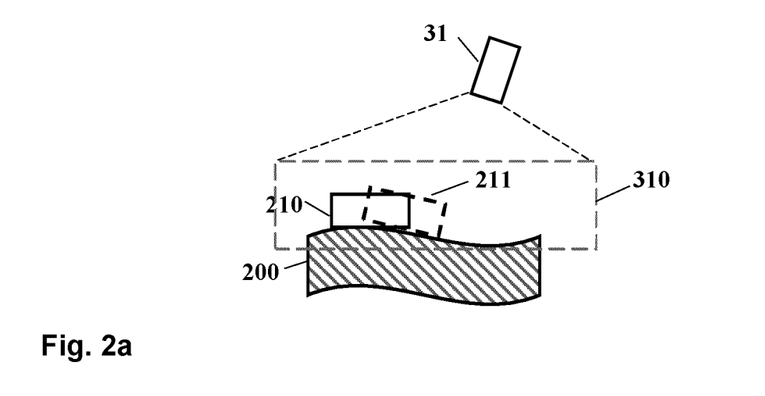
FIGS. 2a and 2b illustrates two possible embodiments of the invention, differing in the position of a camera.

According to a first embodiment, depicted in the side-view of FIG. 2*a*, the camera 31 is positioned so as to capture a scene 310 encompassing a bone target area 200 and the instrumentation 210. The dotted shape 211 represents the planned position of the instrumentation.

Figure 2B:
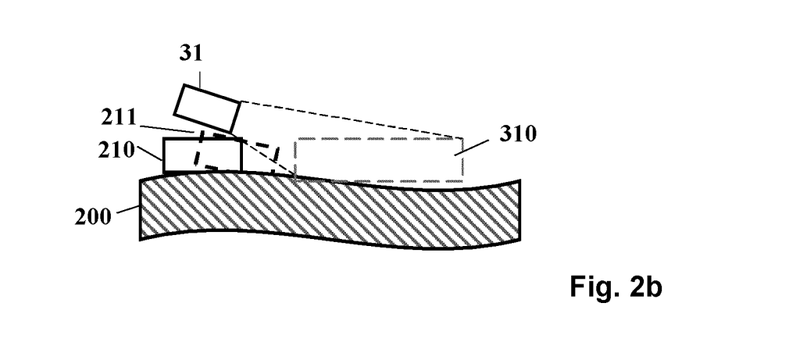

According to a second embodiment, depicted in FIG. 2*b*, the camera 31 is fixed onto the instrumentation itself. It captures a scene 310 comprising the bone target area 200. In some situation, according to the location and orientation of the camera, the captured scene may not comprise any element of the instrumentation, but only the target bone area (and background areas).

As in FIG. 2*a*, the dotted shape 211 represents the planned position of the instrumentation.

Figure 3:
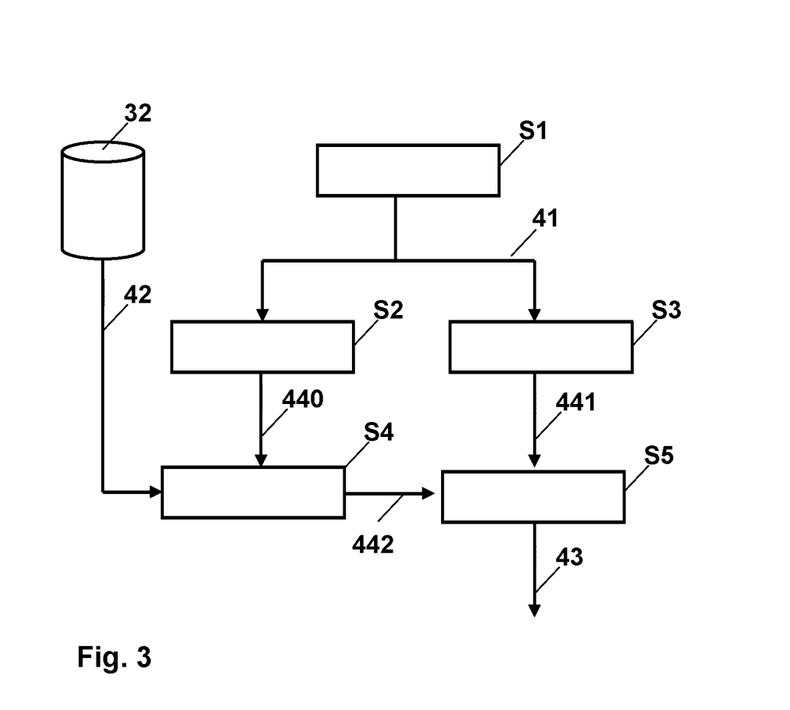
FIG. 3 illustrate a flow chart of a method according to embodiments of the invention.

A method according to embodiments of the invention is depicted on FIG. 3. The skilled person would understand that some deviations can be made from this flow chart, in particular in the order and parallel/sequence nature of the various steps. Also, these steps may be considered as functional only, and provided as separated boxes for clarity only and may not correspond to the actual implementation in a programming language.

Also, this flow-chart may represent only one iteration of a looping procedure, allowing to continuously refresh the data provided to the surgeon.

A first step S1 may thus be the capture of a depth map 41 of a captured scene 310.

As mentioned earlier, the captured scene comprises at least a target bone area. It may also comprise the instrumentation. The depth map associates a depth information to each point of a surface view of the captured scene.

In case the camera is not fixed on the instrumentation, then a step S2 can be provided to determine a positioned shape 440 of this instrumentation from the depth map 41.

According to embodiments of the invention, the determination of the positioned shape 440 of the instrumentation can be based only on the depth map provided by the 3D camera.

According to other embodiments, RGB data provided by RGBD camera can be used, for instance for detecting markers (e.g. ARUCO markers or any other markers available in the art) placed on the instrument. Colour information may be required for an accurate detection of such markers.

Markers, placed on the instruments, may help improving the detection of the positions of the instruments within the captured images. In particular, such markers can be placed during the building of the PSI, so that the relative place of a marker with regard to a PSI is fixed and accurately known, letting no room for any manual misplacement.

However, according to the invention, it is avoided to place markers on the bones because of the additional intraoperative time and complexity that it would imply.

In other words, the determination can make no use of the RGB data provided by a video camera associated (or part of) the 3D camera.

It has been also shown by experiments that image detection algorithms are sensible to the specific lighting conditions of surgery rooms and provides poor performance. Controversially, the range camera techniques are far less sensible to these lighting conditions and show better performances regardless of lighting conditions.

Furthermore, this step of determining a positioned shape 440 of the instruction and, as it will be seen below, to determine a second positioned shape 442 of the target bone area according to this positioned shape 440 is advantageous compared with a direct determination of the target bone area from the depth map.

Indeed, in certain situations where the body incision is small, the portion of the target bone area may be not sufficiently large to allow its correct determination. So, technics based on mapping a digital model of a target area with the portion of target bone area detected in the depth map may fail or may be not precise enough.

According to the invention, instead, the first determination is based on the instrumentation which is usually more visible in the 3D image flow, allowing better tracking and matching. Then, knowing the relative position of the instrumentation (e.g. PSI) with the target bone area, a precise position of the target bone area can be deduced, regardless of the among of target area which is visible within the 3D image flow.

Determining the positioned shape of the instrumentation corresponds to determining a 6 degrees of freedom (6 DoF) vector (the shape of the instrumentation being known). The six degrees of freedom (6-DoF) refer to the freedom of movement of a rigid body in the three-dimensional (3D) space. The 6-DoF pose estimation consists thus in evaluating both the 3D translation and the 3D rotation of this rigid body according to the camera's main coordinate system.

Estimating the pose is still a challenging problem in computer vision and numerous approaches have been proposed and can thus be used to implement this step S2.

In T. Hodan, F. Michel, E. Brachmann, W. Kehl, A. G. Buch, D. Kraft, B. Drost, J. Vidal, S. Ihrke, X. Zabulis, C. Sahin, F. Manhardt, F. Tombari, T. Kim, J. Matas, C. Rother, "BOP: Benchmark for 6D Object Pose Estimation," ECCV 2018, 2018 and in T. Hodan, M. Sundermeyer, B. Drost, Y. Labbe, E. Brachmann, F. Michel, C. Rother, J. Matas, "BOP Challenge 2020 on 6D Object Localization,". ECCV 2020, 2020 it has been assessed and compared several state-of-the-art methods to perform the pose estimation from either RGB images or/and depth maps. From these exhaustive studies, it has been shown that the Point Pair Features (PPF)-based algorithm, first introduced by Drost in 2010, and successively improved by Birdal in 2015, Hinterstoisser in 2016 and Vidal in 2018, was one of the most successful pose estimation algorithms among all model-based approaches, including machine-learning based ones.

References to the PPF algorithm can be found in:

B. Drost, M. Ulrich, N. Navab, and S. Ilic, "Model Globally, Match Locally: Efficient and Robust 3D Object Recognition," IEEE Conf. Comput. Vis. Pattern Recognit. Work., 2010.

T. Birdal and S. Ilic, "Point Pair Features Based Object Detection and Pose Estimation Revisited," Proc.—2015 Int. Conf. 3D Vision, 3DV 2015, pp. 527-535, 2015.

S. Hinterstoisser, V. Lepetit, N. Rajkumar, and K. Konolige, "Going Further with Point Pair Features," ECCV 2017, 2017.

J. Vidal, C. Lin, and R. Marti, "6D Pose Estimation using an Improved Method based on Point Pair Features," Int. Conf. Control. Autom. Robot., 2018.

According to embodiments, the step S2 of determining a positioned shape 440 of the instrumentation from the depth model is based on the PPF algorithm.

As seen earlier, RGB information may also be exploited, if available, in particular for detecting markers, like Aruco markers or other markers available in the art.

The main concept of PPF is to exploit the advantages of both local and global descriptors, and it relies on two phases: (1) an offline phase enabling the a priori global modelling of the object of interest, and (2) an online matching phase allowing the pose estimation of this object in a depth scene.

During the offline step, the features of the object of interest, in our case the instrumentation, are first analysed by computing the following four dimensional vector F for every pair of points of the point cloud describing the object (m1; m2):

$$F(m_1, m_2) = \left( \|\vec{d}\|, \angle(\vec{n_1}, \vec{d}), \angle(\vec{n_2}, \vec{d}), \angle(\vec{n_1}, \vec{n_2}) \right)^T$$

where, $\vec{d}$ is the vector between both points $m_1$ and $m_2$, ($\vec{n_1}$, $\vec{n_2}$) are the normal vectors of these respective points, and $\angle(a, b)$ denotes the angle between vectors a and b.

A hash table storing all the model pairs is then constructed using the discretized PPF, defined by Drost in the above-mentioned article, as index. During the online phase, the pose of the object of interest is then estimated by finding the best match with the hash table regarding the point cloud of the scene. To find this best match, a voting scheme, similar to the Generalized Hough Transform, is used. To do that, the same 4D vector F is computed directly from the scene.

If a similar discretized PPF is found in the model hash table, a vote is casted in a 2D accumulator space. The best pose candidates correspond thus to the highest peaks in this accumulator space. The selected poses are finally clustered such that every pose in one cluster do not differ more than predefined thresholds for both the translation and the rotation. Each cluster will be finally associated with a score corresponding to the sum of the votes of each individual pose contained in this cluster and the best pose is the cluster having the highest score.

According to embodiments of the invention, the improved version of the PPF algorithm proposed by Vidal et al. in the above-mentioned article can be used to determine the positioned shape of the instrumentation from the depth map.

Compared to the original PPF algorithm, several improvements have been added to mitigate noise issues and obtain better recognition performance, such as the use of a novel subsampling step with normal clustering and neighbour pairs filtering, a faster k-d tree neighbour search, a more efficient solution for the quantization, and finally, several additional post-processing steps for re-scoring, refining and filtering the final hypothesis.

To obtain relevant pose estimations, five algorithm's parameters have to be adjusted:
(1) the sampling distance step $d_{dist}$,
(2) the sampling angle step dangle used to compute the discretized PPF,
(3) the number of reference points from the scene used to find the correspondences during the matching,
(4) the clustering distance threshold, and
(5) the clustering angle threshold used for the poses clustering.

Although several recommendations have been given in the literature for the adjustment of four of these parameters (i.e. the sampling angle step dangle, the number of reference points, the clustering distance threshold and the clustering angle threshold), the sampling distance $d_{dist}$ depends on the characteristics of both the object and the depth sensor. According to the literature, the sampling angle step dangle and the clustering angle threshold have to be set to 12°, the number of reference points is 5 and the clustering distance threshold, which has to correspond to 10% of the object diameter, has been fixed to 0.012 m in our case.

In order to find the optimized value for the sampling distance $d_{dist}$, one can assess the fitting performance of the algorithm using a specific score, called Depth Fitting Error (DFE) and defined as the Euclidean distance between the registered instrumentation mesh using PPF and the points from the point cloud provided by the 3D camera associated to this object. 150 scenes have been acquired under different poses. The $d_{dist}$ value providing the lowest mean DFE can then be selected.

According to other embodiments of the invention, the step S2 of determining a positioned shape 440 of the instrumentation from the depth model may be based on ICP algorithm.

Iterative Closest Point (ICP) algorithm is an algorithm employed to minimize the difference between two clouds of points. It has been first proposed in Chen, Yang; Gerard Medioni (1991). "Object modelling by registration of multiple range images". Image Vision Comput. 10 (3): 145-155. doi:10.1016/0262-8856(92)90066-C, and Besl, Paul J.; N. D. Mckay (1992). "A Method for Registration of 3-D Shapes". IEEE Transactions on Pattern Analysis and Machine Intelligence. 14 (2): 239-256. doi: 10.1109/34.121791

A step S3 consists in determining a position element of the target bone area from the same depth map.

According to embodiments, this position element may comprise a first positioned shape 441 of this target bone area from the depth map.

For doing so, similar algorithms can be used as for step S2, for instance.

According to other embodiments a more minimalist approach can be taken, avoiding the use of pose estimation algorithms for the bone. The goal would be to check with the depth camera that the bone surface is theoretically placed in the good position with respect to the PSI.

For doing so, image segmentation can be performed so as to determine the position, in the image, of the bone structure.

As an example, machine learning algorithm can be used, in particular based on Convolutional Neural Networks (CNN), in order to segment bone areas from background areas.

Such a segmentation algorithm has been proposed in He Liu and Ferdinando Rodriguez Y Baena. "Automatic Bone Extraction from Depth Images" in Robotic Assisted Knee Replacement. Proceedings of the 12th Hamlyn Symposium on Medical Robotics, 2019, and as well in Loy Rodas, Decrouez, Bleunven and Cahen, "In-vivo bone segmentation approach for Total Knee Arthroplasty" in EPIC Series in Health Sciences, Volume 4, 2020, or Kaiming He, Georgia Gkioxari, Piotr Dollar, and Ross Girshick. Mask R-CNN. Proceedings of the IEEE International Conference on Computer Vision, pages 2980-2988, 2017.

Mask R-CNN is an object detection and semantic segmentation model. It is based on Region-Based Convolutional Neural Networks (R-CNN). The original goal of R-CNN was to take an input image and produce a set of bounding boxes as output, where each bounding box contains an object and also the category (e.g. bone) of the object. R-CNN as well as Mask R-CNN are for instance further explained in the related Wikipedia page: https://en.wikipedia.org/wiki/Region Based Convolutional Neural Networks Mask R-CNN extends Faster R-CNN to pixel-level image segmentation. The key point is to decouple the classification and the pixel-level mask prediction tasks. Based on the framework of Faster R-CNN, it added a third branch for predicting an object mask in parallel with the existing branches for classification and localization. The mask branch is a small fully-connected network applied to each region of interest, predicting a segmentation mask in a pixel-to-pixel manner.

It combines a feature pyramid network backbone followed by a region proposal network for generating segmentation masks and class predictions at pixel-level, for a given query object within an input image.

A possible implementation can rely on a ResNet-101 architecture as feature extractor backbone model.

The network can be pre-trained by using open-source dataset like COCO ("Common Objects in Context") which is provided by Microsoft and composed of 328 k labelled images.

Then, an additional training can be applied with surgical dataset to fine-tune the weights of the output layers only. Such a procedure allows to not depend on large surgical dataset, which would be difficult (if not impossible) to constitute in practice. This "transfer learning" procedure has shown good performance results according to the above-mentioned article of Loy Rodas et al.

The inventors have further experiences good performance results of such algorithm to determine the positioned shape 441 of the target bone area within the depth map.

For instance, a neural network can be used to segment the areas of the provided points cloud where is located the bone and also the instruments, and based on this segmentation, one can apply PPF for the instruments, and optionally the bone, in order to estimate its/their pose(s).

In order to be probably more robust, embodiments of the invention may make use of markers (like Aruco markers or any other markers available in the art), placed on the PSI, and of the RGB data for the pose estimation of the instrument only (not the bone). However, again, markers are not placed on the bone, because it would need to have a specific marker which would require additional intraoperative time and complexity.

The positioned location of the target bone area determined at this step S3 is called "first" positioned location.

In parallel, a "second" positioned location of the target bone is determined, at step S4, according to the relative positioning 42 of the instrumentation with regard to the target bone area as indicated in the planning.

In case the 3D camera is fixed on said instrumentation, the second positioned shape 442 of said target bone area derives directly from said relative positioning 42.

Indeed, the position (location and orientation) of the camera relatively to the instrumentation can be predetermined data, depending on the design of the instrumentation for instance. Also, the calibration parameters of the 3D camera are known. This information being known, it is straightforward to derive, from the planning, the position of where the target bone should normally be, i.e. the second positioned shape 442.

In case the camera is not fixed on the instrumentation, some additional computing shall be performed, as indicated earlier, because the relative position of the camera with regard to any elements of the captured scene is unknown.

According to embodiments of the invention, this further degree of freedom can be determined by determining the positioned shape 440 of the instrumentation in the depth map, in previously-described step S2. Then the second positioned shape 442 can be determined from both this positioned shape 440 and the relative positioning 42, provided by the planning.

In a step S5, the computer device can determine data representative of the appropriate positioning of the instrumentation on the base of the first positioned shape 441 of the target bone area (calculated in step S3) and of the second positioned shape 442 of the same target bone area as derived or computed from the planned relative positioning 42 (in step S4).

In other words, the data representative of the appropriate positioning of the instrumentation is based on a comparison of planned and measured positioning of the target bone areas.

These data aim in providing to the surgeon some indication on the accuracy of the actual placement of the instrumentation according to the planning.

For instance, a distance map may be provided from the second positioned shape and the position element of the bone's structure. In case a first positioned shape has been determined in step S3, the distance map may comprise point-to-point comparison between the first and second positioned shapes 441, 442. Otherwise, the distance map may be directly computed from the second positioned shape 442 and a point provided by the depth camera (i.e. without estimating the pose of the bone).

As the PPF algorithm provides a model for a shape comprising a set of vertices (i.e. 3D point), both shapes can be compared vertex by vertex. Then, distances can be determined for each vertex.

This distance map may be provided to the surgeon by displaying it as an overlay to the images provided by the 3D camera.

For instance, some colour may be assigned to distance ranges, so that colours represent the accuracy of the assignment: for example, if the distance is above a first threshold, then a "orange" colour can be assigned, if the distance is above a higher threshold, then a "red" colour can be assigned; if the distance is below an acceptable threshold, then a "green" colour can be assigned.

Then, from the depicted colour, the surgeon may immediately understand whether the instrumentation is appropriately placed or not.

In embodiments, when a first positioned shape has be computed in step S3, the computer device may also determine rigid transformation data reflecting error vectors between the first and second positioned shapes. This data may be a 6D vector (translation and rotation) representative of this rigid geometric transform between both shapes.

This transform vector may be provided to the surgeon as guidance of the movement to imply to the instrumentation to correct its position. When the instrumentation is appropriately positioned (in location and in orientation), the transform vector shall be a null vector.

The invention can also be deployed as training facility wherein trainees can practice in mock-up situation and get feedbacks on their skills.

Thanks to the instrumentation (and in particular to PSI), the surgeon is on position to perform cuts with better accuracy.

A person of skill in the art would readily recognize that the computer device would comprises means, or circuitry, like at least one processor; and
at least one memory including computer program code, the at least one memory and computer program code configured to, with the at least one processor, cause the performance of the computer device.

The memory may be, e.g., digital memories, magnetic storage media such as a magnetic disks and magnetic tapes, hard drives, or optically readable digital data storage media.

The computer program code is intended to determine, according to the above-described embodiments, the first and second positioned shapes, 441, 442, the positioned shape 440 of the instrumentation, the data 43 representative of the appropriate positioning, as well as Human-Machine Interface to the surgeon and other additional functions, when run onto the processor(s) of the computer device.

As known to the skilled person, the processor(s) may further run other computed program codes like OS (Operating System) codes, and other modules.

The description and drawings merely illustrate the principles of the invention. It will thus be appreciated that those skilled in the art will be able to devise various arrangements that, although not explicitly described or shown herein, embody the principles of the invention and are included within its spirit and scope. Furthermore, all examples recited herein are principally intended expressly to be only for pedagogical purposes to aid the reader in understanding the principles of the invention and the concepts contributed by the inventor(s) to furthering the art and are to be construed as being without limitation to such specifically recited examples and conditions. Moreover, all statements herein reciting principles, aspects, and embodiments of the invention, as well as specific examples thereof, are intended to encompass equivalents thereof.

The invention claimed is:

1. A computerized system for performing a surgical procedure on a patient, said computerized system comprising a computer device for determining during a surgical procedure an appropriate positioning of an instrumentation on a target bone area of a patient according to a planned relative positioning of said instrumentation to said target bone area defined by a surgical planning, a 3D camera, and a database or memory adapted to store the surgical planning, said computer device comprising;

an interface for receiving from the 3D camera a depth map and RGB data of a captured scene comprising at least said target bone area and said instrumentation;

a computing tool comprising at least one processor; and at least one memory including computer program code, the at least one memory and computer program code configured to, with the at least one processor, cause the computer device to perform determining a position element of said target bone area only from said depth map, comprising a first positioned shape corresponding to a measured positioning of said target bone area; determining a positioned shape of said instrumentation from said depth map and the RGB data, wherein markers placed on said instrumentations are detected using the RGB data, determining a second positioned shape of said target bone area according to said positioned shape, corresponding to a planned positioning and said planned relative positioning, and determining data representative of said appropriate positioning based on said second positioned shape and said first positioned shape, wherein said determining comprises computing a distance map between said second positioned shape and said first positioned shape;

a human-machine interface for providing said data as feedback, wherein said human-machine interface is configured to display the distance map as an overlay to the images provided by the 3D camera, so as to allow a user check and improve an accuracy of an actual placement of said instrumentation according to the surgical planning.

2. The computer system according to claim 1, wherein said data comprises rigid transformation data reflecting error vectors between said first and second positioned shapes.

3. The computer system according to claim 1, further adapted to determine said positioned shape of said instrumentation according to a Point-Pair Feature algorithm.

4. A method for determining during a surgical procedure an appropriate positioning of an instrumentation on a target bone area according to a planned relative positioning of said instrumentation to said target bone area defined by a surgical planning, said method being implemented by a computer device integrated into a computerized system for performing a surgical procedure on a patient, said computerized system comprising a 3D camera, a database adapted to store the surgical planning, said computer device comprising at least one processor; and at least one memory including computer program code, the at least one memory and computer program code configured to, with the at least one processor, cause the computer device to perform the method, an interface with the 3D camera, and a human-machine interface, said method comprising:

receiving a depth map and RGB data of a captured scene comprising at least said target bone area and said instrumentation, from said 3D camera through the interface;

determining a position element of said target bone area only from said depth map, comprising a first positioned shape corresponding to a measured positioning of said target bone area;

determining a positioned shape of said instrumentation from said depth map and the RGB data, wherein markers placed on said instrumentations are detected using the RGB data;

determining a second positioned shape corresponding to a planned positioning of said target bone area according to said positioned shape and said planned relative positioning;

determining data representative of said appropriate positioning based on said second positioned shape and said first positioned shape, wherein said determining comprises computing a distance map between said second positioned shape and said first positioned shape;

providing said data to said human-machine interface, said human-machine interface being configured to display the distance map as an overlay to the images provided by the 3D camera, as feedback so as to allow a user check and improve an accuracy of an actual placement of said instrumentation according to the surgical planning.

5. The method according to claim 4, wherein said data comprises rigid transformation data reflecting error vectors between said first and second positioned shapes.

6. A computer readable medium storing a machine-executable program of instructions configured to perform a method for determining during a surgical procedure an appropriate positioning of an instrumentation on a target bone area according to a relative positioning of said instrumentation to said target bone area defined by a surgical planning, said method being implemented by a computer device integrated into a computerized system for performing a surgical procedure on a patient, said computerized system comprising a 3D camera, a database adapted to store the surgical planning, said computer device comprising at least one processor; and at least one memory including the machine-executable program of instructions, the at least one memory and the machine-executable program of instructions configured to, with the at least one processor, cause the computer device to perform:

receiving a depth map of a captured scene comprising at least said target bone area and said instrumentation, from said 3D camera;

determining a position element of said target bone area only from said depth map, comprising a first positioned shape corresponding to a measured positioning of said target bone area;

determining a positioned shape of said instrumentation from said depth map and the RGB data, wherein markers placed on said instrumentations are detected using the RGB data;

determining a second positioned shape corresponding to a planned positioning of said target bone area according to said positioned shape and said planned relative positioning;

determining data representative of said appropriate positioning based on said second positioned shape and said first positioned shape, wherein said determining comprises computing a distance map between said second positioned shape and said first positioned shape;

providing said data to a human-machine interface, configured to display the distance map as an overlay to the images provided by the 3D camera, as feedback so as to allow a user check and improve an accuracy of an actual placement of said instrumentation according to the surgical planning.

* * * * *